United States Patent [19]

Kempeni et al.

[11] Patent Number: 5,332,571
[45] Date of Patent: Jul. 26, 1994

[54] PRODUCTS CONTAINING A LITHIUM SALT AND A TUMOR NECROSIS FACTOR

[75] Inventors: Joachim Kempeni, Neustadt-Duttweiler; Michael Kluge, Kallstadt; Walter Fiers, Destelbergen, all of Fed. Rep. of Germany

[73] Assignee: BASF Aktiengesellschaft, Ludwigshafen, Fed. Rep. of Germany

[21] Appl. No.: 613,518
[22] PCT Filed: Feb. 27, 1990
[86] PCT No.: PCT/EP90/00324
  § 371 Date: Nov. 2, 1990
  § 102(e) Date: Nov. 2, 1990
[87] PCT Pub. No.: WO90/10455
  PCT Pub. Date: Sep. 20, 1990

[30] Foreign Application Priority Data
Mar. 7, 1989 [DE] Fed. Rep. of Germany ....... 3907244

[51] Int. Cl.$^5$ ..................... A61K 45/06; A61K 37/02
[52] U.S. Cl. .................................. 424/85.1; 530/351
[58] Field of Search ............... 530/351; 424/85.1, 677, 424/709, 715, 722; 514/561, 578

[56] References Cited

FOREIGN PATENT DOCUMENTS

| 0100641 | 7/1982 | European Pat. Off. . |
| 0187991 | 7/1986 | European Pat. Off. . |
| WO86/04606 | 8/1986 | PCT Int'l Appl. . |
| 03489 | 6/1987 | World Int. Prop. O. . |

OTHER PUBLICATIONS

International Preliminary Examination Report.
European Journal of Biochemistry, vol. 152, 1985.
Beyaert et al, *Proc. Natl. Acad. Sci. USA* 36: 9494–9498 (Dec. 1989).
Kleinerman et al, *J. of Leukocyte Biology* 46: 484–492 (Nov. 1989).
Stein et al, *Cancer* 48:2696–2701 (Dec. 15, 1981).

Primary Examiner—Jeffrey E. Russel
Assistant Examiner—P. Lynn Touzeau
Attorney, Agent, or Firm—Herbert B. Keil

[57] ABSTRACT

The enhancement of the antitumor action of tumor necrosis factor by lithium salts is described.

2 Claims, 5 Drawing Sheets

PRODUCTS CONTAINING A LITHIUM SALT AND A TUMOR NECROSIS FACTOR

The present invention relates to products containing a lithium salt and a tumor necrosis factor, and to the use of lithium salts for enhancing the action of tumor necrosis factors.

It has already been disclosed that tumor necrosis factor a (TNF-α) or tumor necrosis factor β (TNF-β, also called lymphotoxin), as well as muteins of these two substances, can inhibit the growth of cancer cells, cf. Eur. J. Biochem. 152, 515, 1985; EP 187 991, WO 86/04 606, EP 100 641.

It has now been found that the action of tumor necrosis factors can be increased by administration of lithium salts.

The invention relates to products containing a lithium salt and a tumor necrosis factor as combination product for simultaneous or sequential use for the treatment of malignant tumors in humans and their associated phenomena.

The invention furthermore relates to the use of lithium salts for enhancing the action of exogenously administered or endogenously induced tumor necrosis factors.

The term malignant tumors means tumors of the hemopoietic organs, especially leukemias and lymphomas, as well as malignant tumors of various organs. The malignant tumors include, in particular, tumors of the lungs, of the gastrointestinal tract, of the urogenital tract, of the breast and of the skin and of appendages thereof.

The associated phenomena in cases of malignant tumors include, in particular, malignant effusions into body cavities as a consequence of these tumors.

The term tumor necrosis factor means TNF-α, TNF-β (lymphotoxin) and the active muteins thereof.

The tumor necrosis factor is, as a rule, used in a daily amount of from 1 to 500 μg/m² of body surface area, especially in a daily amount of from 40 to 400 μg/m². In this connection, administration is intravenous, subcutaneous, intraperitoneal or intra- or peritumoral.

Suitable lithium salts are, in particular, the carbonate, D,L-hydrogenaspartate, sulfate, orotate, acetate and the chloride. The lithium salts are administered orally, intravenously, intraperitoneally or intra- or peritumorally in an amount such that the level of Li+ ions in the blood is between 0.4 and 1.8 mmol, but in particular between 0.7 and 1.4 mmol.

The tumor necrosis factor and the lithium salt can be used in known pharmaceutical administration forms, cf. Rote Liste 1988, Nos. 70223 to 70227, EP-A 209 030.

The superiority of the novel combination therapy was shown in vitro and in vivo as follows:

In Vitro Experiments 24 hours before the treatment, the cells were streaked in a concentration of from 5 to $10^3$ cells/flask in a cell-specific medium on microtiter plates. Then several TNF dilutions were added. To test LiCl, this was added to the cells 2 hours before the treatment with TNF in various concentrations. After an incubation time of 72 hours at 37° C., the adherent cells were fixed and stained for 15 minutes with a solution which contained 0.5% (w/v) crystal violet, 4% (v/v) formaldehyde, 30% (v/v) ethanol and 0.17% (w/v) NaCl. The flasks were thoroughly rinsed with tap water, and the adherent cells were then detached in 33% (v/v) acetic acid (0.1 ml/test tube). The liberated dye was measured by spectrophotometry using an Immunoreader NJ-2000 (Nippon Intermed, Tokyo, Japan).

Figure 1:
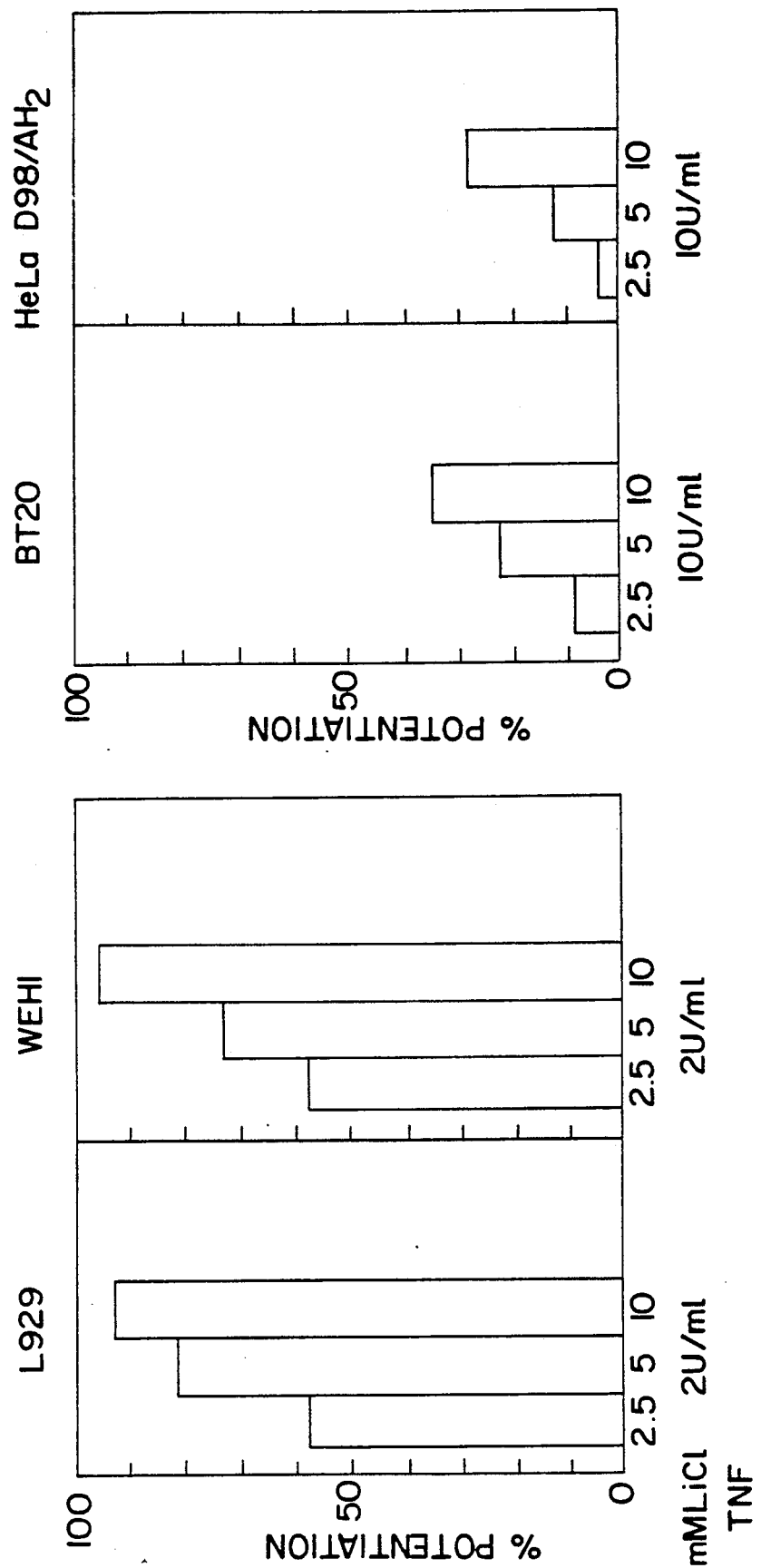
FIG. 1 shows the enhancement of the TNF-related cytotoxicity by LiCl with various malignant cell lines.
Figure 2:
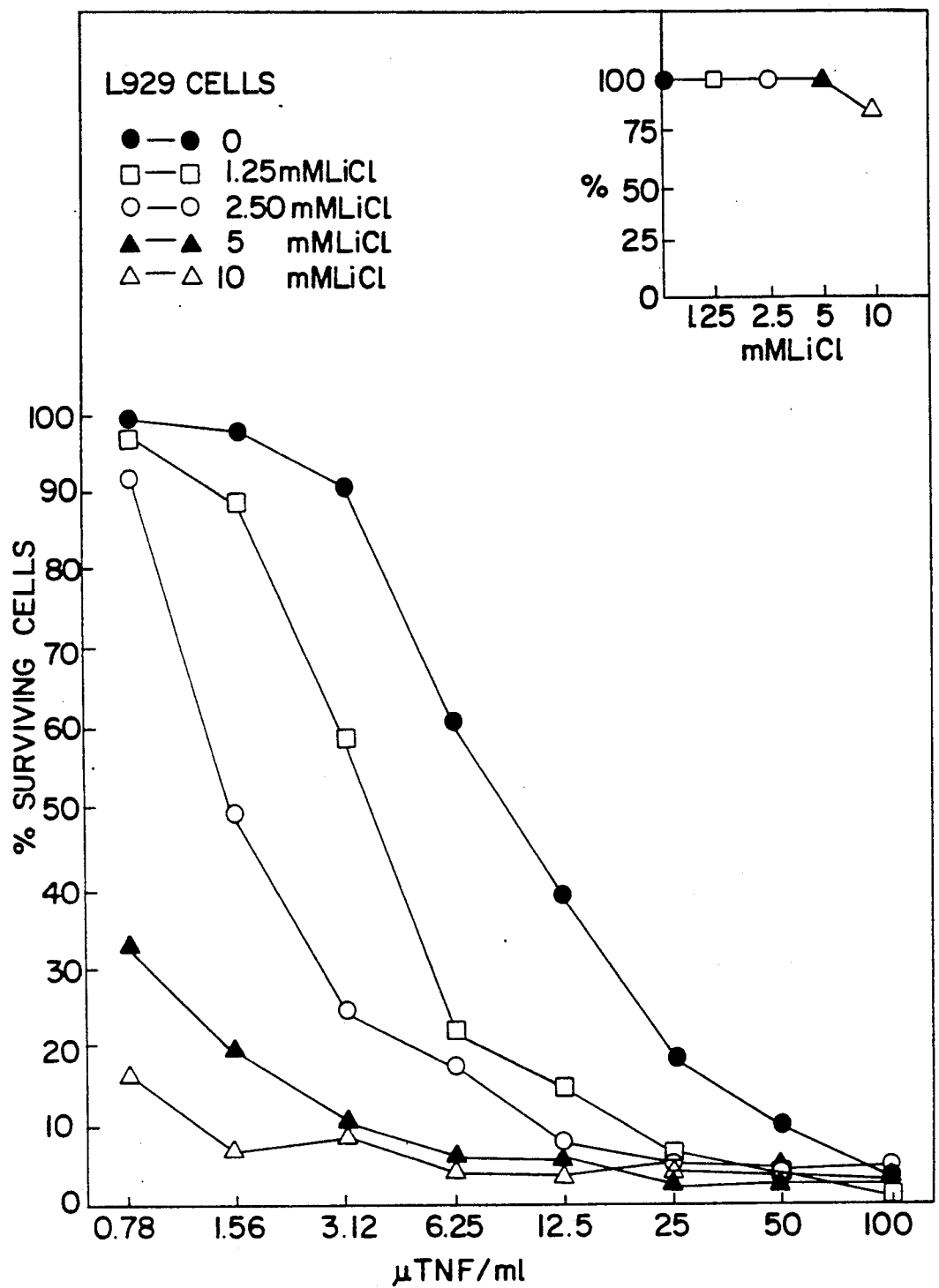
FIG. 2 shows the dose-dependent action of the LiCl on the cytotoxicity of L929 cells caused by TNF.

The influence of LiCl on the cytolytic/cytostatic activity of TNF was investigated on two cell lines of mice (L929 and WHI 164, clone 13) and five cell lines of humans (MCF7-AZ, ME180, Bt20 and HeLa D98(AH2). All the cell lines were sensitive to TNF. LiCl enhanced the cytotoxic action of TNF on all the mouse cell lines and three of the investigated cell lines of humans in a dosedependent manner (FIG. 1). In the presence of LiCl, there was almost complete killing of cells at TNF concentrations which alone showed virtually no action (FIG. 2).

In Vivo Experiments

Subcutaneous (s.c.) injection of $10^6$ L-929 cells in 6-week old female nude mice (nu/nu; IFA-CREDO, Brussels, Belgium) brought about rapid growth of non-invasive tumors. The tumors were treated peritumorally (daily s.c. injection in the proximity of the tumor site but outside the node) with TNF and/or LiCl over several periods of 5 days at an interval of 2 days. The TNF doses were increased weekly, while the LiCl dose was kept constant at 1 mg/mouse. Compared with TNF alone, the action of the combination of TNF and LiCl was very pronounced (FIG. 3; LiCl alone showed no action). From the second week onward, some tumors additionally became necrotic after the treatment with TNF or TNF/LiCl. Apart from one mouse (complete disappearance of the tumor after 2 weeks of combination therapy), in both cases the growth inhibition was not complete, however. No side effects occurred on longer combination therapy (for several weeks). The mice treated with TNF survived longer than the control mice; however, the animals survived considerably longer after a combination therapy (FIG. 4).

Figure 5:
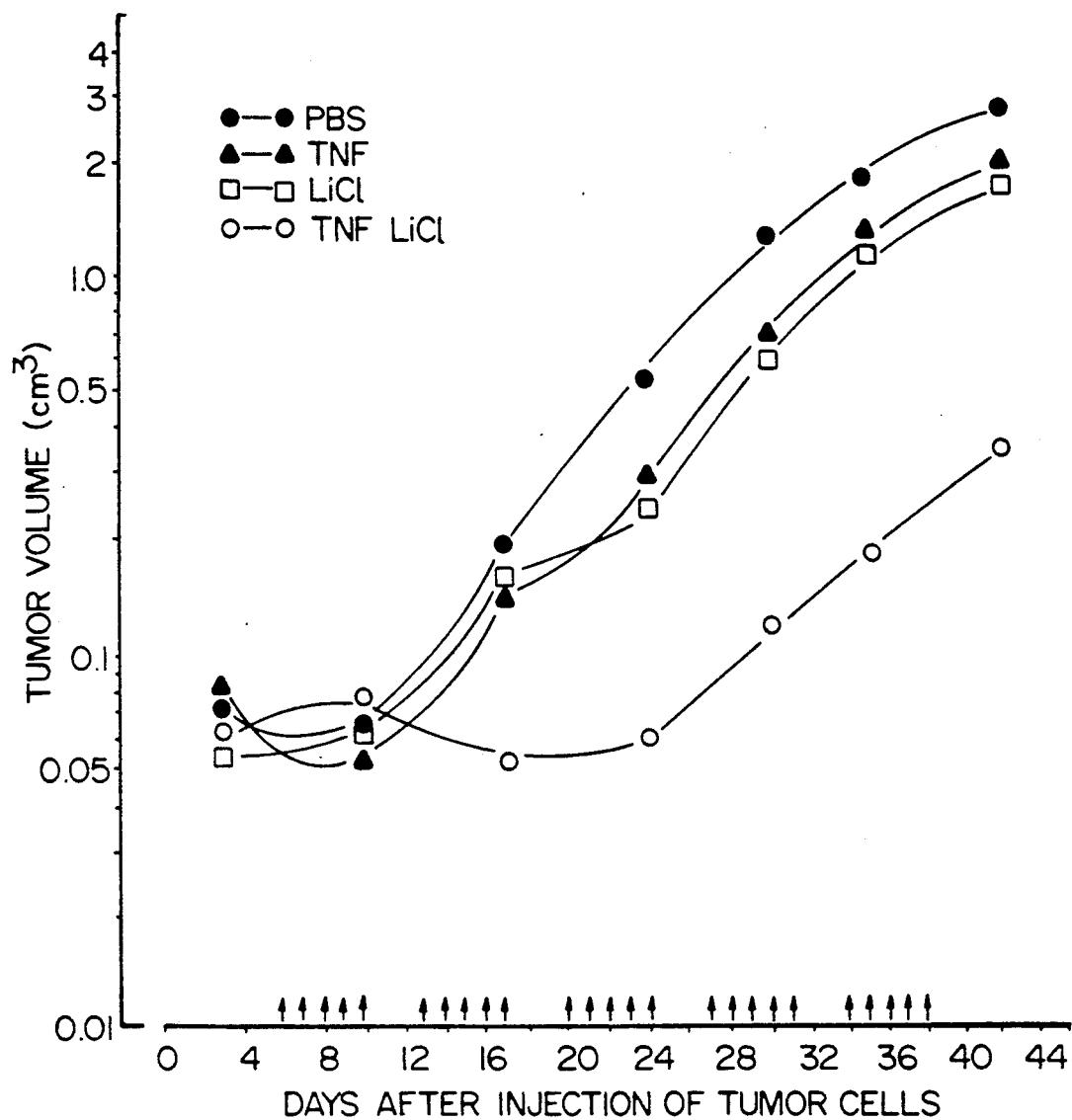
FIG. 5 shows the effects of the treatment with TNF and/or LiCl on the growth of s.c. Hela D98/AH2 tumors in nu/nu mice.

In addition, nude mice received s.c. injections of HeLa D/98/AH2 cells ($3 \times 10^6$) which generated slower growing tumors. The same protocol as described above was employed. TNF alone showed little effect on tumor growth in this case too. By contrast, a combination therapy with LiCl brought about growth inhibition, while no necrosis was visible. After longer treatment with the combination, two (of six) mice were completely tumor-free (FIG. 5).

LEGENDS TO FIGURES FIGS. 1 TO 5

FIG. 1

Enhancement of the TNF-related cytotoxicity by LiCl with various malignant cell lines The cells were tested in an in vitro assay as described above. The percentage potentiation is depicted for an increasing LiCl concentration at constant TNF concentration.

$$\text{Percentage potentiation} = \left[1 - \frac{Abs(TNF + LiCl)}{Abs(TNF)}\right] \times 100$$

(Abs corresponds to the absorption at 590 nm for the fixed and stained cells after treatment with the substances in parentheses).

LiCl alone had no action whatever on the viability of the cells. The values from a representative experiment are shown.

FIG. 2

Dose-dependent action of LiCl on the cytotoxicity of L929 cells caused by TNF

The cells were tested in the in vitro assay described above. The percentage survival was plotted in comparison with the increasing TNF concentrations. For each LiCl concentration the percentage survival corresponds to the cell staining determined after the treatment with TNF+LiCl, expressed as percentage of the cell staining determined in cultures which were treated with LiCl but not with TNF (=100%). The figure inserted top right shows the influence of LiCl on cell growth and survival in the absence of TNF.

FIG. 3

Effects of treatments with TNF and TNF+LiCl on the growth of s.c. L929 tumors in nu/nu mice The tumor size (product of the largest diameters at right angles) is plotted in comparison with the time (days after injection of the tumor cells). All the mice (six per group) received a peritumoral injection of 0.1 ml of a mixture of the two substances on the days marked by an arrow. TNF was administered in the following doses: 5 µg ( 1st week ), 10 µg ( 2nd and 3rd week ), 15 µg (4th week) and 20 µg (5th week); the concentration of LiCl was 1 mg/injection in all cases.

FIG. 4

Figure 3:
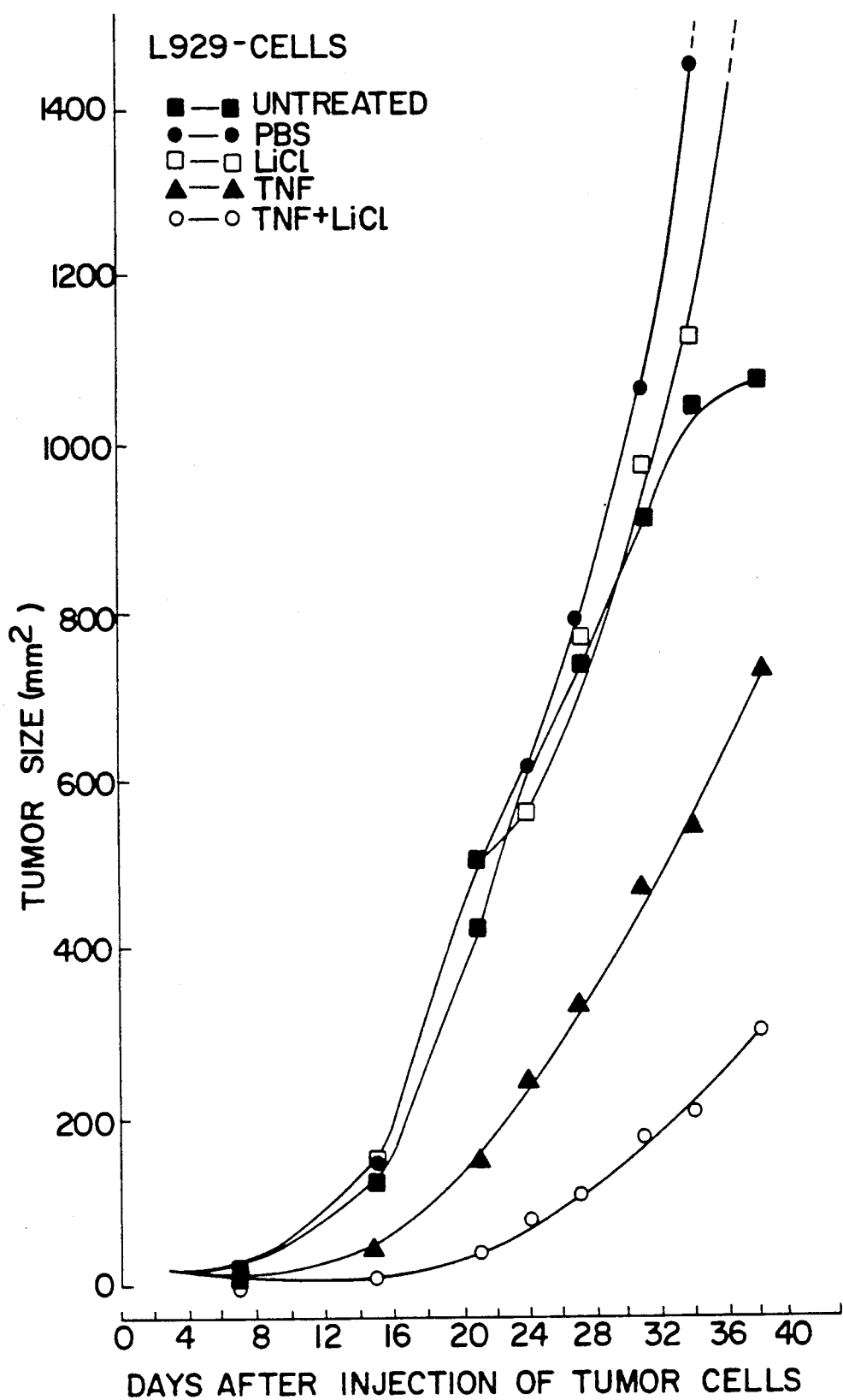
FIG. 3 shows the effects of treatments with TNF and TNF+LiCl on the growth of s.c. L929 tumors in nu/nu mice.
Figure 4:
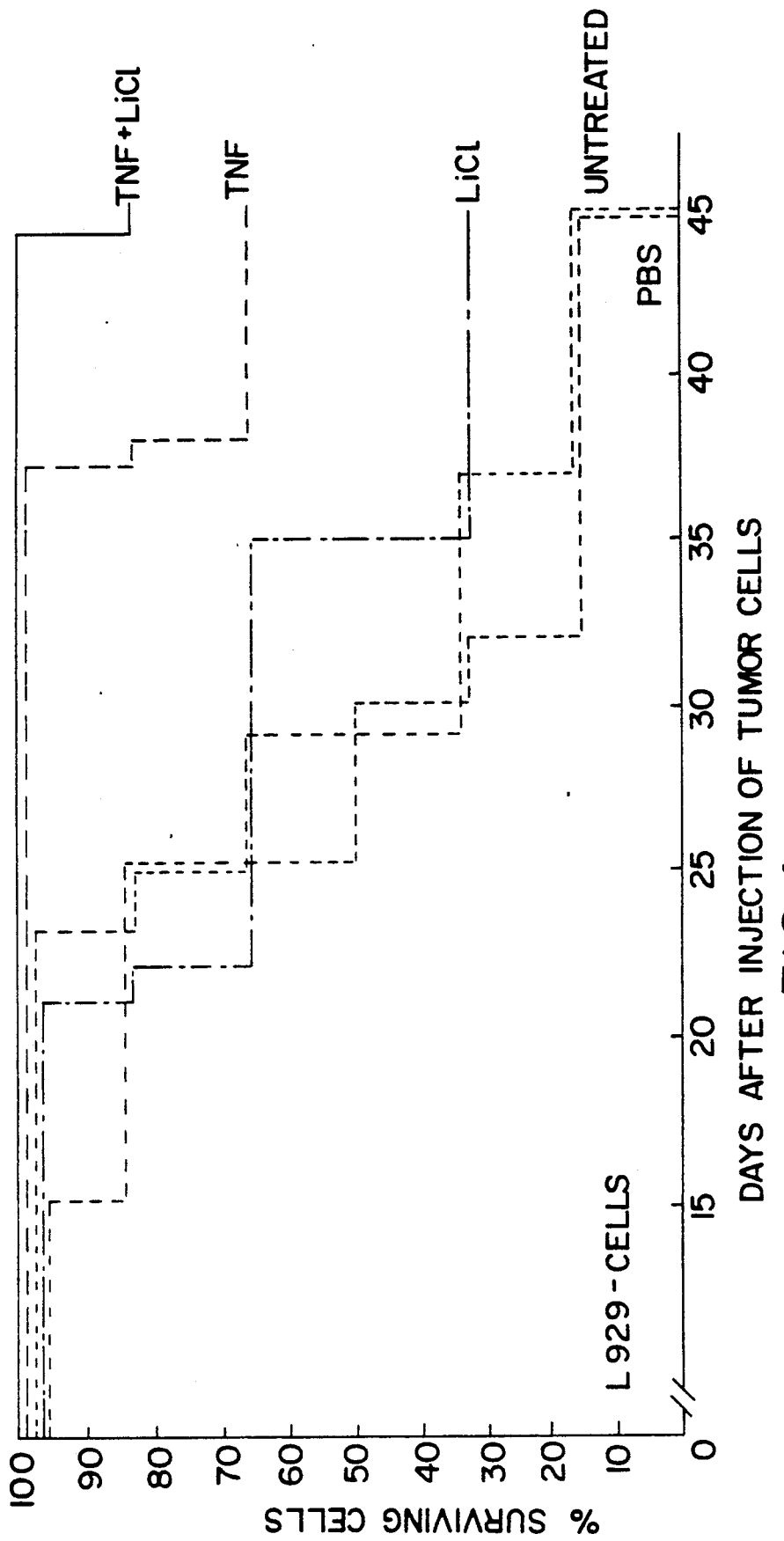
FIG. 4 shows the survival of mice which received s.c. injections of L929 cells and treatment with TNF and/or LiCl.

Survival of mice which received s.c. injection of L929 cells and treatment with TNF and/or LiCl The results apply to the mice detailed in the legend to FIG. 3.

FIG. 5

Effects of the treatment with TNF and/or LiCl on the growth of s.c. HeLa D98/AH2 tumors in nu/nu mice The tumor size was calculated by the method of Attia and Weiss ( 1966 ) ( 0.4 ab$^3$) and is drawn as semilogarithmic scale in comparison with the time (days after injection of the tumor cells). All the mice (6 per group) received peritumoral injection of 0.1 ml of a solution of TNF or LiCl or of a mixture of TNF and/or LiCl on the days marked by an arrow. TNF was administered in the following doses: 10 µg (1st week), 15 µg (2nd and 3rd week) and 25 µg (4th and 5th week); the concentration of LiCl was 1 mg/injection in all cases.

What is claimed:

1. In a product for the treatment of malignant tumors in humans and their associated phenomena, which product comprises a combination product for simultaneous or sequential use and which product includes a tumor necrosis factor, the improvement wherein the combination product includes a lithium salt.

2. In the treatment of malignant tumors in humans malignant infusions into the body cavities wherein a combination of products is administered exogenously or endogenously, simultaneously or sequentially, and which combination includes a tumor necrosis factor, the improvement wherein the combination includes a lithium salt.

* * * * *